(12) United States Patent
Courtemanche et al.

(10) Patent No.: US 10,368,741 B2
(45) Date of Patent: Aug. 6, 2019

(54) METHOD OF AND SYSTEM FOR PROCESSING SIGNALS SENSED FROM A USER

(71) Applicants: VALORISATION-RECHERCHE, LIMITED PARTNERSHIP, Montreal (CA); VALORISATION GESTION, LIMITED PARTNERSHIP, Montreal (CA)

(72) Inventors: Francois Courtemanche, Montreal (CA); Marc Fredette, Candiac (CA); Sylvain Senecal, Carignan (CA); Pierre-Majorique Leger, St-Lambert (CA); Aude Dufresne, Montreal (CA); Vanessa Georges, Montreal (CA); Elise Labonte-Lemoyne, Montreal (CA)

(73) Assignees: VALORISATION-RECHERCHE, LIMITED PARTNERSHIP, Montreal (CA); VALORISATION GESTION, LIMITED PARTNERSHIP, Montreal (CA)

( * ) Notice: Subject to any disclaimer, the term of this patent is extended or adjusted under 35 U.S.C. 154(b) by 173 days.

(21) Appl. No.: 15/552,788

(22) PCT Filed: Feb. 25, 2016

(86) PCT No.: PCT/IB2016/051028
§ 371 (c)(1),
(2) Date: Aug. 22, 2017

(87) PCT Pub. No.: WO2016/135661
PCT Pub. Date: Sep. 1, 2016

(65) Prior Publication Data
US 2018/0035886 A1 Feb. 8, 2018

Related U.S. Application Data

(60) Provisional application No. 62/121,552, filed on Feb. 27, 2015.

(51) Int. Cl.
A61B 3/113 (2006.01)
A61B 3/00 (2006.01)
(Continued)

(52) U.S. Cl.
CPC ............ *A61B 3/113* (2013.01); *A61B 3/0025* (2013.01); *A61B 5/0205* (2013.01); *A61B 5/16* (2013.01);
(Continued)

(58) Field of Classification Search
USPC .................................................. 382/100, 103
See application file for complete search history.

(56) References Cited

U.S. PATENT DOCUMENTS

| 7,774,052 | B2 * | 8/2010 | Burton | A61B 5/0476 600/544 |
| 8,898,344 | B2 * | 11/2014 | Frank | G06F 17/28 710/5 |

(Continued)

FOREIGN PATENT DOCUMENTS

DE 102013017820 A1 4/2015

OTHER PUBLICATIONS

Extended European Search Report with regard to the counterpart EP Patent Application No. 16754848.6 completed Nov. 22, 2018.
(Continued)

*Primary Examiner* — Ishrat I Sherali
(74) *Attorney, Agent, or Firm* — BCF LLP

(57) ABSTRACT

A system for and a method of processing signals sensed from a user. The method comprises accessing positions of a line of sight of the user over a time frame, a first set of data associated with a first physiological signal and a second physiological signal. The method further comprises executing, by a processor, for at least one position of the positions of the line of sight of the user, identifying a first subset of (Continued)

data from the first set of data, identifying a second subset of data from the second set of data, associating the at least one position with the first subset of data and the second subset of data and causing to generate, by a machine-learning algorithm, a predicted value reflective of a pattern associated with the user. The method also comprises storing the predicted value associated with the at least one position.

20 Claims, 8 Drawing Sheets

(51) Int. Cl.
    *A61B 5/16*     (2006.01)
    *A61B 5/00*     (2006.01)
    *A61B 5/0205*     (2006.01)
    *G06F 3/01*     (2006.01)
    *G06N 20/00*     (2019.01)
    *G16H 50/20*     (2018.01)

(52) U.S. Cl.
    CPC ............ *A61B 5/163* (2017.08); *A61B 5/7267* (2013.01); *G06F 3/013* (2013.01); *G06F 3/015* (2013.01); *G06N 20/00* (2019.01); *G16H 50/20* (2018.01)

(56) References Cited

U.S. PATENT DOCUMENTS

| | | | | |
|---|---|---|---|---|
| 9,833,184 | B2* | 12/2017 | Derchak | A61B 5/16 |
| 10,182,736 | B2* | 1/2019 | Coleman | A61B 5/0482 |
| 2008/0221401 | A1 | 9/2008 | Derchak et al. | |
| 2010/0292545 | A1* | 11/2010 | Berka | A61B 5/048 600/301 |
| 2014/0347265 | A1 | 11/2014 | Aimone et al. | |
| 2016/0029965 | A1* | 2/2016 | Simon | A61B 5/1103 600/301 |
| 2017/0316463 | A1* | 11/2017 | Pielot | G06Q 30/0269 |

OTHER PUBLICATIONS

International Search Report with regard to PCT/IB2016/051028 dated Jun. 15, 2016.
Dufresne et al., "Physiological Measures, Eye Tracking and Task Analysis to Track User Reactions in UGC", Proceedings of 7th International Conference on Methods and Techniques in Behavioural Research, Aug. 2010, pp. 218-221.
Bednarik et al., "What do you want to do next: a novel approach for intent prediction in gaze-based interaction", Proceedings of the Symposium of Eye Tracking Research and Applications, Mar. 2012, pp. 83-90.
Judd et al., "Learning to predict where humans look", IEEE 12th International Conference on Computer Vision (ICCV), Sep. 2009, pp. 2106-2113.
Courtemanche et al., "Activity recognition using eye-gaze movements and traditional interactions", Interacting with Computers, May 2011, vol. 23, pp. 202-213.
English Abstract for DE102013017820 retrieved on Espacenet on May 15, 2018.

\* cited by examiner

METHOD OF AND SYSTEM FOR PROCESSING SIGNALS SENSED FROM A USER

CROSS-REFERENCE TO RELATED APPLICATION

This International Application claims priority from U.S. Provisional Patent Application Ser. No. 62/121,552, filed on Feb. 27, 2015, entitled "Method and product for visualizing the emotions of a user" the entire content of which is incorporated herein by reference.

FIELD

The present technology relates to systems and methods for processing signals sensed from a user. In particular, the systems and methods aim at associating positions of a line of sight of the user with physiological signals and/or generating a predicted value based on the physiological signals.

BACKGROUND

Physiological measures are increasingly used in many different areas of human-computer interaction (HCI) to infer knowledge about the affective and cognitive states of users. Technology currently available allows various physiological signals reflecting physiological measures to be sensed from users. For example, but without being limitative, the physiological signals may include (1) sweating rates measured from electrical conductance of the skin by an Electro Dermal Activity (EDA) sensor, (2) pulse rates measured from pulse sensor and/or (3) brain activity measured by electroencephalogram (EEG) electrodes to be placed on a user's scalp to detect brain waves of the user. The recent developments now allow to access physiological signals from wearable technologies, such as, for example, connected watches, which may include various sensors, such as, for example, (1) EDA sensors and/or (2) pulse sensors.

Once acquired, the physiological signals may be processed to serve various purposes. For example, physiological measures may be used in video games studies to measure boredom and/or game experience. Various applications may also be envisioned, including, but not limited to, providing intelligent tutoring systems leveraging physiological signals to improve adaptation of pedagogical interventions to user needs during learning sessions. Other applications may also be envisioned and may become apparent to the person skilled in the art of the present technology.

Even though various developments have been recently made in the field of inferring knowledge about the affective and cognitive states of users, improvements remain desirable as the analysis of physiological measures to extract meaningful information remains a challenge. In particular, extracting meaningful information from physiological signals typically requires expert knowledge which, in at least some instances, may not even be sufficient to associate physiological signals with user behaviour and/or assess, with a metric, a user state based on such physiological signals.

SUMMARY

It is an object of present technology to provide improvements, in particular improvements aiming at improving (1) correlating physiological signals sensed from a user and positions of a line of sight of the user and/or (2) generating a predicted value reflective of a pattern associated with the user. In some embodiments, the pattern may be a psychological construct such as an emotion associated with the user 170, a cognitive load associated with the user 170, a stress associated with the user 170 and an attention associated with the user 170 and/or a flow associated with the user 170.

The present technology arises from an observation made by the inventor(s) that positions of the line of sight of the user may be associated with a first subset of data having being identified from a first set of data associated with a first physiological signal sensed from the user and with a second subset of data having being identified from a second set of data associated with a second physiological signal sensed from the user. In some embodiments, the first subset of data is identified based on a first latency and a first duration dynamically determined based on at least one of a category of the first physiological signal and a category of a pattern which is being assessed. In some embodiments, the second subset of data is identified based on a second latency and a second duration dynamically determined based on at least one of a category of the second physiological signal and the category of the pattern which is being assessed. In some embodiments, a machine-learning algorithm operated by a processor may be relied upon to generate a predicted value associated with the pattern based on the first subset of data and the second subset of data.

Thus, in one aspect, various implementations of the present technology provide computer-implemented method of processing signals sensed from a user, the method comprising:

accessing, from a non-transitory computer readable medium, positions of a line of sight of the user over a time frame;

accessing, from the non-transitory computer readable medium, a first set of data associated with a first physiological signal sensed from the user over the time frame;

accessing, from the non-transitory computer readable medium, a second set of data associated with a second physiological signal sensed from the user over the time frame;

executing, by a processor, for at least one position of the positions of the line of sight of the user:

identifying a first subset of data from the first set of data based on a first latency and a first duration, the first latency and the first duration being associated with the first physiological signal, the first latency and the first duration being dynamically determined based on a pattern category;

identifying a second subset of data from the second set of data based on a second latency and a second duration, the second latency and the second duration being associated with the second physiological signal, the second latency and the second duration being dynamically determined based on the pattern category;

associating the at least one position with the first subset of data and the second subset of data;

causing to generate, by a machine-learning algorithm, a predicted value reflective of a pattern associated with the user, the predicted value being generated by the machine-learning algorithm based on the first subset of data and the second subset of data, the predicted value being associated with the at least one position; and storing, in the non-transitory computer readable medium, the predicted value associated with the at least one position.

In some aspects, prior to identifying a first subset of data from the first set of data based on a first latency and a first duration, the method comprises determining the pattern category.

In some further aspects, causing to generate, by the machine-learning algorithm, the predicted value further comprises accessing a database comprising a set of training data having been, at least partially, previously generated by the machine-learning algorithm.

In some aspects, at least one of the first subset of data and the second subset of data is compared, by the machine-learning algorithm, with the set of training data to generate the predicted value.

In some further aspects, the predicted value is reflective of at least one of an intensity of the pattern and amplitude of the pattern.

In some aspects, the at least one position is associated with a pixel of a screen.

In some further aspects, the method further comprises, generating, by the processor, a set of surrounding predicted values based on the predicted value, each one of the surrounding value of the set of surrounding values being associated with a corresponding pixel surrounding the pixel associated with the at least one position.

In some aspects, the set of surrounding predicted values is generated based on a statistical distribution.

In some further aspects, executing, by the processor, the steps of identifying the first subset of data and identifying the second subset of data is carried out for each one of the positions of the line of sight of the user.

In some aspects, causing to generate, by the machine-learning algorithm, the predicted value reflective of the pattern associated with the user is carried out for each one of the positions of the line of sight of the user.

In some further aspects, storing, in the non-transitory computer readable medium, the predicted value associated with the at least one position comprises storing, in the non-transitory computer readable medium, predicted values associated with corresponding positions.

In some aspects, the method further comprises generating, by the processor, a heat map representing the predicted values, each one of the predicted values being positioned on the heat map based on its corresponding position.

In some further aspects, prior to executing, by the processor, the steps of identifying the first subset of data and identifying the second subset of data, the method comprises synchronizing the first physiological signal, the second physiological signal and the at least one position.

In some aspects, prior to accessing, from the non-transitory computer readable medium, the positions of the line of sight of the user over the time frame, the method comprises (1) receiving, from a sensor, an eye tracking signal; and (2) generating, by the processor, the positions based on the eye tracking signal.

In some further aspects, prior to accessing, from the non-transitory computer readable medium, the positions of the line of sight of the user over a time frame, the method comprises (1) receiving, from a first sensor, the first physiological signal; and (2) receiving, from a second sensor, the second physiological signal.

In some aspects, the pattern is a psychological construct and the pattern category is a category of psychological construct.

In other aspects, various implementations of the present technology provide a computer-based system, such as, for example, but without being limitative, an electronic device comprising at least one processor and a memory storing program instructions for processing signals sensed from a user, the program instructions being executable by one or more processors of the computer-based system to carry out one or more of the above-recited methods.

In the context of the present specification, unless expressly provided otherwise, an "electronic device", a "server", a "remote server", and a "computer-based system" are any hardware and/or software appropriate to the relevant task at hand. Thus, some non-limiting examples of hardware and/or software include computers (servers, desktops, laptops, netbooks, etc.), smartphones, tablets, network equipment (routers, switches, gateways, etc.) and/or combination thereof.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, an "indication" of an information element, a "physiological signal", a "position of a line of sight" may be the information element itself or a pointer, reference, link, or other indirect mechanism enabling the recipient of the indication to locate a network, memory, database, or other computer-readable medium location from which the information element may be retrieved. For example, an indication of a file could include the file itself (i.e. its contents), or it could be a unique file descriptor identifying the file with respect to a particular file system, or some other means of directing the recipient of the indication to a network location, memory address, database table, or other location where the file may be accessed. As one skilled in the art would recognize, the degree of precision required in such an indication depends on the extent of any prior understanding about the interpretation to be given to information being exchanged as between the sender and the recipient of the indication. For example, if it is understood prior to a communication between a sender and a recipient that an indication of an information element will take the form of a database key for an entry in a particular table of a predetermined database containing the information element, then the sending of the database key is all that is required to effectively convey the information element to the recipient, even though the information element itself was not transmitted as between the sender and the recipient of the indication.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Thus, for example, it should be understood that, the use of the terms "first set of data" and "third set of data" is not intended to imply any particular order, type, chronology, hierarchy or ranking (for example) of/between the server, nor is their use (by itself) intended imply that any "second set of data" must necessarily exist in any given situation. Yet as another example, it should be understood that, the use of the terms "first physiological signal" and "third physiological signal" is not intended to imply, unless specified otherwise, any particular order, type, chronology, hierarchy or ranking (for example) of/between the physiological signals, nor is their use (by itself) intended imply that any "second physiological signal" must necessarily exist in any given situation. Further, as is discussed herein in other contexts, reference to a "first" element and a "second" element does not preclude the two elements from being the same actual real-world element. Thus, for example, in some instances, a "first" server and a "second" server may be the same software and/or hardware, in other cases they may be different software and/or hardware.

Implementations of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

Figure 1:
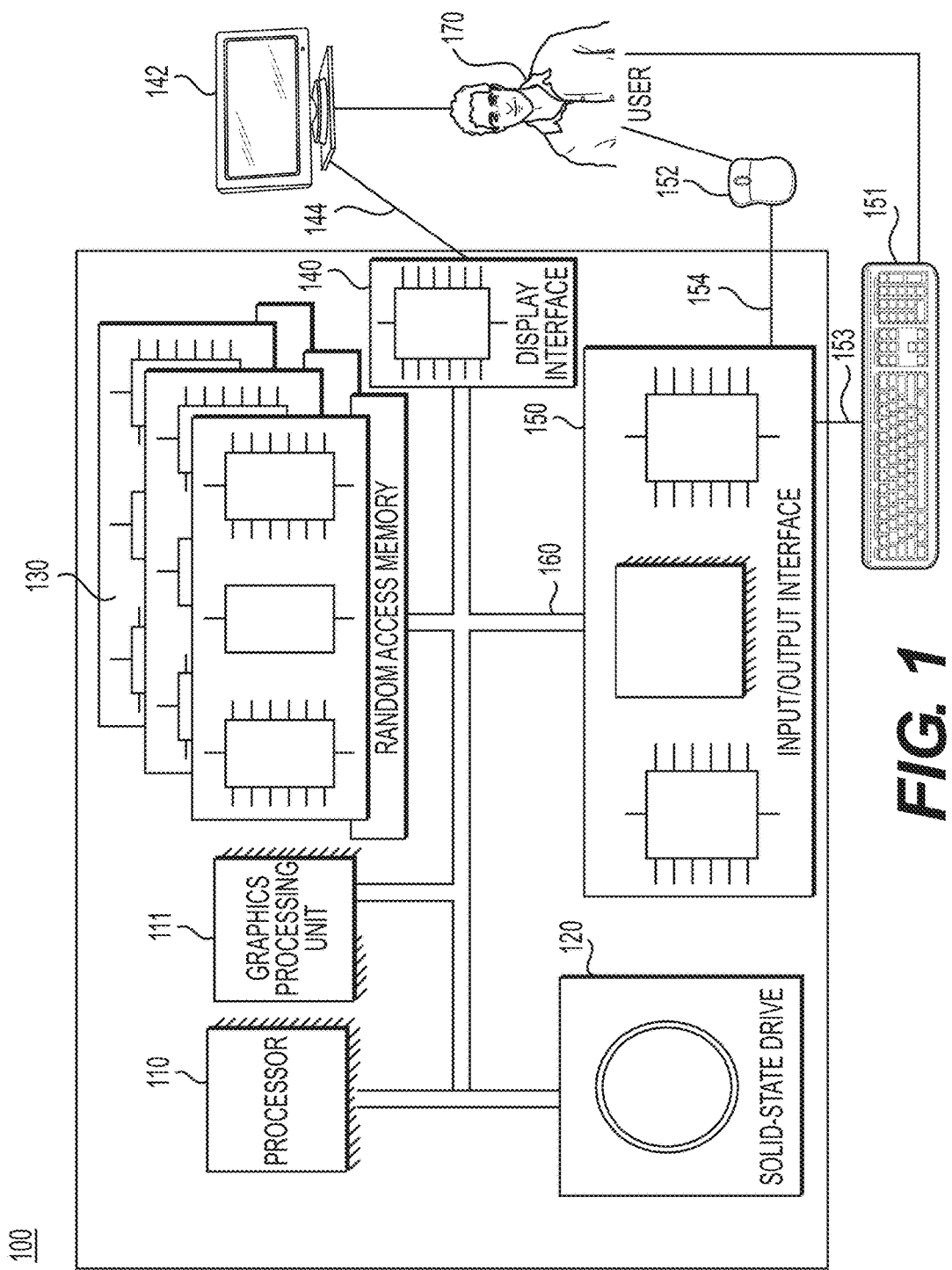
FIG. 1 is a diagram of a computer system suitable for implementing the present technology and/or being used in conjunction with implementations of the present technology.

It should also be noted that, unless otherwise explicitly specified herein, the drawings are not to scale.

DETAILED DESCRIPTION

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology and are included within its spirit and scope.

Furthermore, as an aid to understanding, the following description may describe relatively simplified implementations of the present technology. As persons skilled in the art would understand, various implementations of the present technology may be of a greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Moreover, all statements herein reciting principles, aspects, and implementations of the present technology, as well as specific examples thereof, are intended to encompass both structural and functional equivalents thereof, whether they are currently known or developed in the future. Thus, for example, it will be appreciated by those skilled in the art that any block diagrams herein represent conceptual views of illustrative circuitry embodying the principles of the present technology. Similarly, it will be appreciated that any flowcharts, flow diagrams, state transition diagrams, pseudocode, and the like represent various processes which may be substantially represented in computer-readable media and so executed by a computer or processor, whether or not such computer or processor is explicitly shown.

The functions of the various elements shown in the figures, including any functional block labeled as a "processor" or a "graphics processing unit", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. In some embodiments of the present technology, the processor may be a general purpose processor, such as a central processing unit (CPU) or a processor dedicated to a specific purpose, such as a graphics processing unit (GPU). Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown.

With these fundamentals in place, we will now consider some non-limiting examples to illustrate various implementations of aspects of the present technology.

Referring to FIG. 1, there is shown a computer system 100 suitable for use with some implementations of the present technology, the computer system 100 comprising various hardware components including one or more single or multi-core processors collectively represented by processor 110, a graphics processing unit (GPU) 111, a solid-state drive 120, a random access memory 130, a display interface 140, and an input/output interface 150.

Communication between the various components of the computer system 100 may be enabled by one or more internal and/or external buses 160 (e.g. a PCI bus, universal serial bus, IEEE 1394 "Firewire" bus, SCSI bus, Serial-ATA bus, etc.), to which the various hardware components are electronically coupled. The display interface 140 may be coupled to a monitor 142 (e.g. via an HDMI cable 144) visible to a user 170, and the input/output interface 150 may be coupled to a touchscreen (not shown), a keyboard 151 (e.g. via a USB cable 153) and a mouse 152 (e.g. via a USB cable 154), each of the keyboard 151 and the mouse 152 being operable by the user 170.

According to implementations of the present technology, the solid-state drive 120 stores program instructions suitable for being loaded into the random access memory 130 and executed by the processor 110 and/or the GPU 111 for processing signals sensed from a user. For example, the program instructions may be part of a library or an application.

Figure 2:
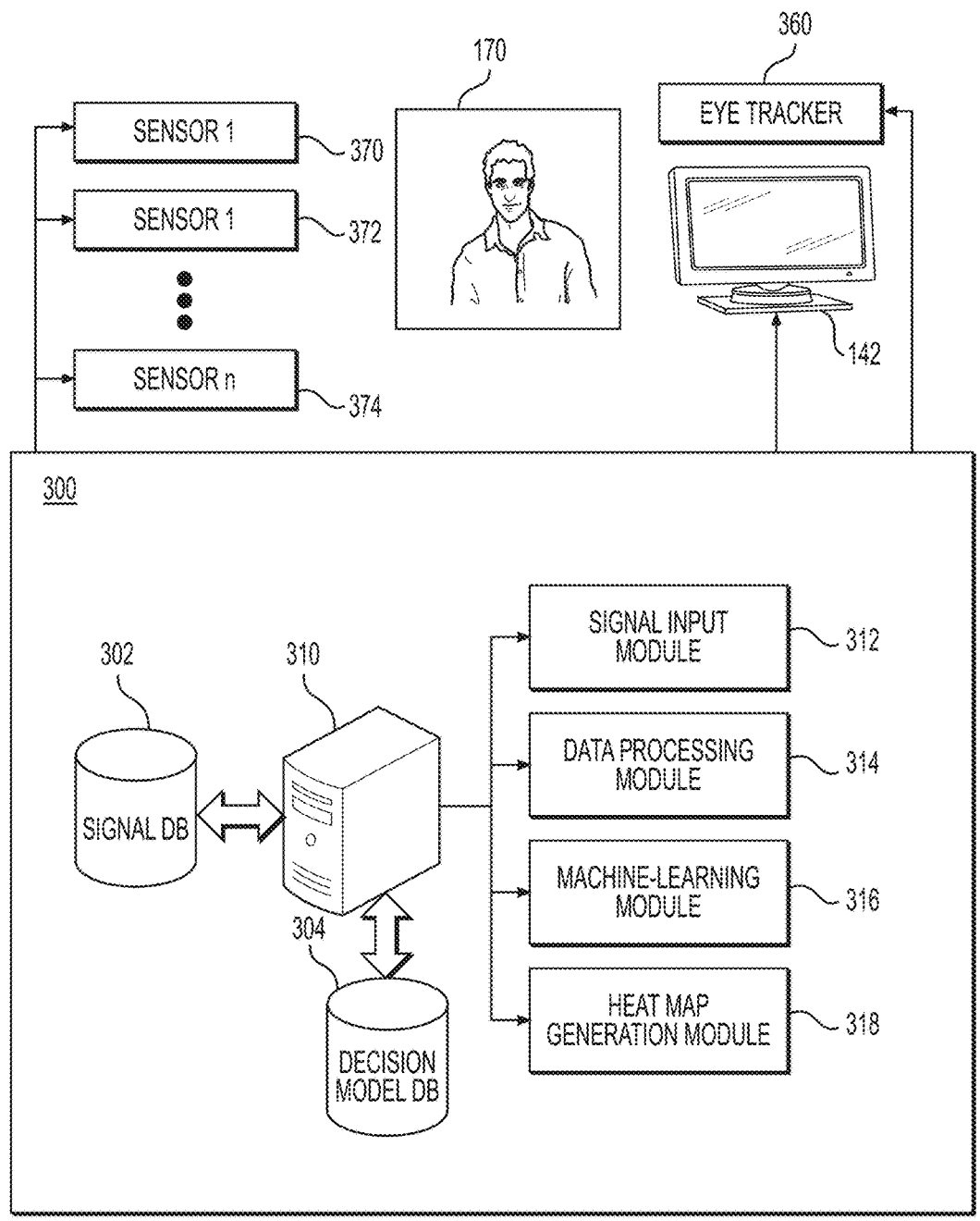
FIG. 2 is a diagram of a computing environment in accordance with an embodiment of the present technology.

In FIG. 2, there is shown a computing environment 300 suitable for use with some implementations of the present technology. The networked computing environment 300 comprises an electronic device 310. The electronic device 310 may (but not necessarily) be associated with a user 170 and, as such, can sometimes be referred to as a "client device". It should be noted that the fact that the electronic device 310 is associated with the user 170 does not need to suggest or imply any mode of operation—such as a need to log in, a need to be registered or the like.

The implementation of the electronic device 310 is not particularly limited, but as an example, the electronic device 310 may be implemented as a personal computer (desktops, laptops, netbooks, etc.), a wireless communication device (a cell phone, a smartphone, a tablet and the like), as well as network equipment (a server, a router, a switch, or a gateway). The electronic device 310 comprises hardware and/or software and/or firmware (or a combination thereof), as is known in the art, to execute a various software modules such, but not limited to, a signal input module 312, a data processing module 314, a machine-learning module 316 and/or a heat map generation module 318. The modules 312, 314, 316 and 318 will be described in greater details below.

The electronic device 310 may be coupled to a communications network (not shown). In some non-limiting embodiments of the present technology, the communications network can be implemented as the Internet. In other embodiments of the present technology, the communications network can be implemented differently, such as any wide-area communications network, local-area communications network, a private communications network and the like.

How the communications network may be implemented is not particularly limited and will depend on how the electronic device 310 is implemented. Merely as an example and not as a limitation, in those embodiments of the present technology where the electronic device 302 is implemented as a wireless communication device (such as a smart-phone), the communications network can be implemented as a wireless communication link (such as but not limited to, a 3G communications network link, a 4G communications network link, a Wireless Fidelity, or WiFi® for short, Bluetooth® and the like). In those examples, where the electronic device 310 is implemented as a notebook computer, the communications network can be either wireless (such as the Wireless Fidelity, or WiFi® for short, Bluetooth® or the like) or wired (such as an Ethernet based connection).

It should be expressly understood that implementations for the electronic device 310, and the communications network are provided for illustration purposes only. As such, those skilled in the art will easily appreciate other specific implementational details for the electronic device 310 and the communications network. As such, by no means, examples provided herein above are meant to limit the scope of the present technology.

In some embodiments, the electronic device 310 may be implemented as a server. The server can be implemented as a conventional computer server. In an example of an embodiment of the present technology, the server can be implemented as a Dell™ PowerEdge™ Server running the Microsoft™ Windows Server™ operating system. Needless to say, the server can be implemented in any other suitable hardware and/or software and/or firmware or a combination thereof. In some non-limiting embodiment of present technology, the server may be a single server. In alternative non-limiting embodiments of the present technology, the functionality of the server may be distributed and may be implemented via multiple servers.

The server may be communicatively coupled (or otherwise has access) to one or more of the modules 312, 314, 316 and 318. Under such embodiments, one or more of the modules 312, 314, 316 and 318 may be partially or totally controlled remotely. In some embodiments, the one or more of the modules 312, 314, 316 and 318 may virtualized in a cloud computing environment accessible and controllable from a remote device, such as, but not limited to, a mobile device. Under such embodiment, the one or more of the modules 312, 314, 316 and 318 may defined a service offered to user as a software as a service (SaaS).

In some embodiments, the computing environment 300 comprises a first sensor 370, a second sensor 372 and a third sensor 374. Each one of the first sensor 370, the second sensor 372 and the third sensor 374 may be wired to the electronic device 310 and/or connected wirelessly to the electronic device 310, for example, but without being limitative, via Wireless Fidelity, or WiFi® for short, Bluetooth® or the like. Each one of the first sensor 370, the second sensor 372 and the third sensor 374 may be implemented as a "stand alone" device or be part of another device, such as being part of an electronic device embedding one or more sensors. For example, one or more of the first sensor 370, the second sensor 372 and the third sensor 374 may be embedded within a wearable device, such as, but without being limited to, a connected watch or a virtual/augmented reality helmet in which case the wearable device may communicate wirelessly with the electronic device 310. In some embodiments, the wearable device may also implement partially or totally the features of the electronic device 310 in which case the wearable device is the electronic device 310. Other variations may also be envisioned without departing from the scope of the present technology.

In some other embodiments, the first sensor 370, the second sensor 372 and/or the third sensor 374 may be connected to a synchronization device (not shown) allowing synchronization of signals generated by the first sensor 370, the second sensor 372 and/or the third sensor 374. In some alternative embodiments, a synchronisation module may directly be embedded in the electronic device 310.

Each one of the first sensor 370, the second sensor 372 and/or the third sensor 374 may sense one or more physiological signals from the user 170. As an example, but without being limitative, the first sensor 370, the second sensor 372 and/or the third sensor 374 may sense sweating rates measured from electrical conductance of the skin of the user 170, pulse rates and/or brain waves of the user 170. As such, the first sensor 370, the second sensor 372 and/or the third sensor 374, may take various forms, including, but not limited to a Galvanic Skin Response (GSR) sensor, a pulse rate sensor and/or electroencephalogram (EEG) electrodes to be placed on a scalp of the user 170. Other variations of sensors may also be envisioned such as pupil dilation, electrocardiogram (ECG), muscular activity (electromyogram EMG), Functional Near-Infrared Spectroscopy (fNIRS), respiration rate, skin temperature, body movements In some embodiments, the first sensor 370 senses a first physiological signal from the user 170, for example a sweating rate, the second sensor 372 senses a second physiological signal from the user 170, for example a pulse rate and the third sensor 374 senses a third physiological signal from the user 170, for example a EEG signal. This embodiment aims at exemplifying implementations of the present technology and shall not be construed as being limitative. Multiple variations may be envisioned, including variations wherein the first sensor 370 and the second sensor 372 senses a same physiological signal and the third sensor 374 senses a physiological signal different from the physiological signal sensed by the first sensor 370 and the second sensor 372.

As depicted in FIG. 2, the computing environment 300 comprises an eye tracker 360 and a display 142 (which may be similar to the display 142 of FIG. 1). In some embodiments, the eye tracker 360 aims at acquiring positions of a line of sight of the user. In some embodiments, the line of sight of the user may also be referred to as a gaze. For the purpose of the present document, "line of sight of the user" and "gaze" may be used interchangeably without departing from the scope of the present technology. In some embodiments, the eye tracker 360 may be referred to as a sensor generating an eye tracking signal. In some embodiments, in addition to acquiring positions of a line of sight of the user 170, the eye tracker 360 may also sense other signals, for example by determining a pupil size of the user 170. In such embodiment, the pupil size may be one of the physiological signals. As a person skilled in the art of the present technology, the eye tracker 360 may be implemented using various technologies allowing computing of a direction of an eye of the user 170. In some embodiments, the eye tracker 360 may determine a position of the line of sight of the user 170 on the display 142, when the user 142 is presented with stimuli on the display 142. As an example, the eye tracker 360 may be implemented using the eye tracker X-60 from Tobii Technology, the ETG 2w glasses from SMI from SensoMotoric Instruments, or the embedded webcam in the Galaxy S6 cellphone.

In some embodiments, the display 142 may be implemented as a conventional monitor displaying static images or videos in 2D and/or in 3D. In some alternative embodiments, the display 142 may not display images per se but instead projects images on a surface. Under such embodiments, the display 142 may be an image/video projector. In yet some other embodiments, the display 142 may be a virtual/augmented reality helmet wherein two display devices may be combined to present the user 170 with a more immersive experience than a conventional monitor. It should also be noted that, in some embodiments, the eye tracker 360 and the display 142 may be combined into one device, for example a virtual/augmented reality helmet embedding displaying capabilities and tracking of positions of the line of sight of the user 170 while the user 170 is wearing the helmet.

In some embodiments, the positions of the line of sight of the user 170 may be understood as a position on a surface defined by the display 142. As a result, when a stimulus presented to the user 170 on the display 142 is an image and/or a video, a position of the line of sight of the user 170 may be a point and/or an area of the image and/or the video which may be expressed by means of coordinates (i.e., x and/or y and/or z). In some embodiment, a position may be a point and/or an approximation of a point. In some embodiments, the point may be defined by one or more pixels of the display 142. In some other embodiments, a position may be an area and/or an approximation of an area. In some embodiments, the area may be defined by one or more pixels of the display 142.

Referring back to the electronic device 310, the modules 312, 314, 316 and 318 will be described in greater details in connection with the description of the first sensor 370, the second sensor 372, the third sensor 374, the eye tracker 360 and the display 142. Each one of the modules 312, 314, 316 and 318 may be implemented via software instructions implemented various steps described in conjunction with the description of FIG. 8. In some other embodiments, the modules 312, 314, 316 and 318 may be implemented via specific hardware or via a combination of hardware and software. Each one of the modules 312, 314, 316 and 318 may be hosted on the electronic device 310 or may be distributed across multiple devices.

The signal input module 312 may receive signals from one or more of the first sensor 370, the second sensor 372, the third sensor 374 and the eye tracker 360. In some embodiments, the signals may be sets of data associated with one or more physiological signals and/or positions of the line of sight of the user 170. In some embodiments, the signal input module 312 may receive signals which are then converted into one or more sets of data. In some embodiments, the positions of the line of sight of the user 170 and the sets of data associated with the physiological signals are associated with a time frame. In such embodiments, the time frame is defined as a time window having a start time (t1) and an end time (t2). The time frame is therefore defined as a time interval bounded by t1 and t2. In some embodiments, a set of positions of the line of sight of the user 170 and the sets of data associated with the physiological signals are defined so as to cover a same time frame. In other words, the positions of the line of sight of the user 170 and the sets of data associated with the physiological signals are being recorded simultaneously so that the positions and the sets of data may be later correlated. Even though reference is made to "over the time frame", it should be understood that each one of the positions and the sets of data may each be recorded over a different time window, in which case "over the time frame" would be defined as subset of the different time windows sharing at least a time frame in common. Making reference to "the time frame" allows establishing for, a given time comprised between t1 and t2, a position and values of the physiological signals associated with the given time.

In some embodiments, the signal input module 312 stores the positions and/or the sets of data into signal database 302 hosted in a non-transitory computer readable medium such as the random access memory 130 of FIG. 1 so that the positions and/or the sets of data may become instantaneously available to the data processing module 314 for further processing. In some alternative embodiments, the signal database 302 may be stored in a non-transitory computer readable medium which may be more permanent data storage, such as the solid-state drive 120 of FIG. 1.

As previously mentioned, the data processing module 314 may access the positions of the line of sight of the user 170 and the sets of data associated with physiological signals from a non-transitory computer readable medium. The non-transitory computer readable medium may have been populated by the signal input module 312. In some embodiments, the data processing module 31 may correlate physiological signals sensed from a user and positions of a line of sight of the user. The data processing module 314 may also generate, or cause to generate (for example via the machine-learning module 316) a predicted value reflective of a pattern associated with the user 170. In some embodiments, the pattern may be a psychological construct also referred to as a construct of interest. In some embodiments, the construct of interest may be an emotion associated with the user 170, a cognitive load associated with the user 170, a stress associated with the user 170, an attention associated with the user 170, a visual load associated with the user 170, a vigilance associated with the user 170, and/or a flow associated with the user 170. As the person skilled in the art of the present technology may appreciate other examples of construct of interest represented by the pattern may be envisioned without departing from the scope of the present technology.

In some embodiments, the data processing module 314 allows, for a given position of the line of sight of the user 170, identifying a first subset of data from the first set of data associated with the first physiological signal and identifying a second subset of data from the second set of data associated with the second physiological signal. The data processing module 314 relies on latencies and durations dynamically determined for the first subset and for the second subset. In some embodiments, the latencies and durations are determined based on a pattern category (e.g., a particular psychological construct such as a cognitive load) and/or a psychological signal category (e.g., a sweating rate, a pulse rate, etc. . . . ). As a result the first subset and the second subset may differ in terms of start times and end times. The first subset may represent a first segment of the first physiological signal having a start time and an end time selected as such that it properly reflects the measured metric of a given psychological construct for a given position of the line of sight of the user 170 even though the position may not necessarily be synchronous with the second subset. In a similar fashion, the second subset may represent a second segment of the second physiological signal having a start time and an end time selected as such that it properly reflects the measured metric of the given psychological construct for a given position of the line of sight of the user 170 even though the position may not necessarily be synchronous with the first subset. This feature of the data processing module 314 aims at taking into consideration that emotions and/or cognitions require physiological adjustments stemming from multiple responses patterns, different physiological signal may present various durations and/or latencies for a given stimulus. More details will be provided as to how the first subset and the second subset are identified is provided in connection with the descriptions of FIGS. 3 and 4.

In some embodiments, the data processing module 314 may also associate a given position with corresponding first subset of data and second subset of data. The data processing module 314 may also cause the machine-learning module 316 to generate a predicted value reflective of a pattern associated with the user. In some embodiments, the predicted value may be a metric allowing assessing a particular psychological construct of the user 170 whom is being assessed. The predicted value may take various forms, including intensity or a value associated with a scale such as the valence or arousal scale. Other types of metrics or scales may also be used without departing from the scope of the present technology and may become apparent to the person skilled in the art of the present technology. In some embodiments, the data processing module 314 may also store the predicted value in a non-transitory computer readable medium.

In some embodiments, the machine-learning module 316 may be controlled by the data processing module 314 so at to generate the predicted value based on the first subset of data and the second subset of data generated by the data processing module 314. In some embodiments, the machine-learning module 316 implements a machine-learning algorithm, such as, but without being limited to, a neural network, a support vector machine, a decision tree, a Gaussian classifier, a logistic regression, which may have been previously trained on a set of data. In the embodiment depicted at FIG. 2, the set of data takes the form of a decision model database 304 which may be hosted on the electronic device 310 or accessible remotely. In some embodiments, the set of data may have been previously generated by the machine-learning algorithm.

In some embodiments, the predicted value generated by the machine-learning module 316 may be processed by the heat map generation module 318 to generate a heat map to be presented to the user 170, presented to another user or stored for later usage. In some embodiments, the heat map generation module 318 may generate a set of surrounding predicted values based on the predicted value, each one of the surrounding value of the set of surrounding values being associated with a corresponding pixel surrounding the pixel associated with the at least one position associated with the generated predicted value. In some embodiments, the heat map generation module 318 may rely on various distribution models, such as, but not limited to, a Gaussian distribution, to generate the set of surrounding predicted values. More details will be provided as to how the heat map is generated is provided in connection with the descriptions of FIGS. 5, 6 and 7.

Figure 3:
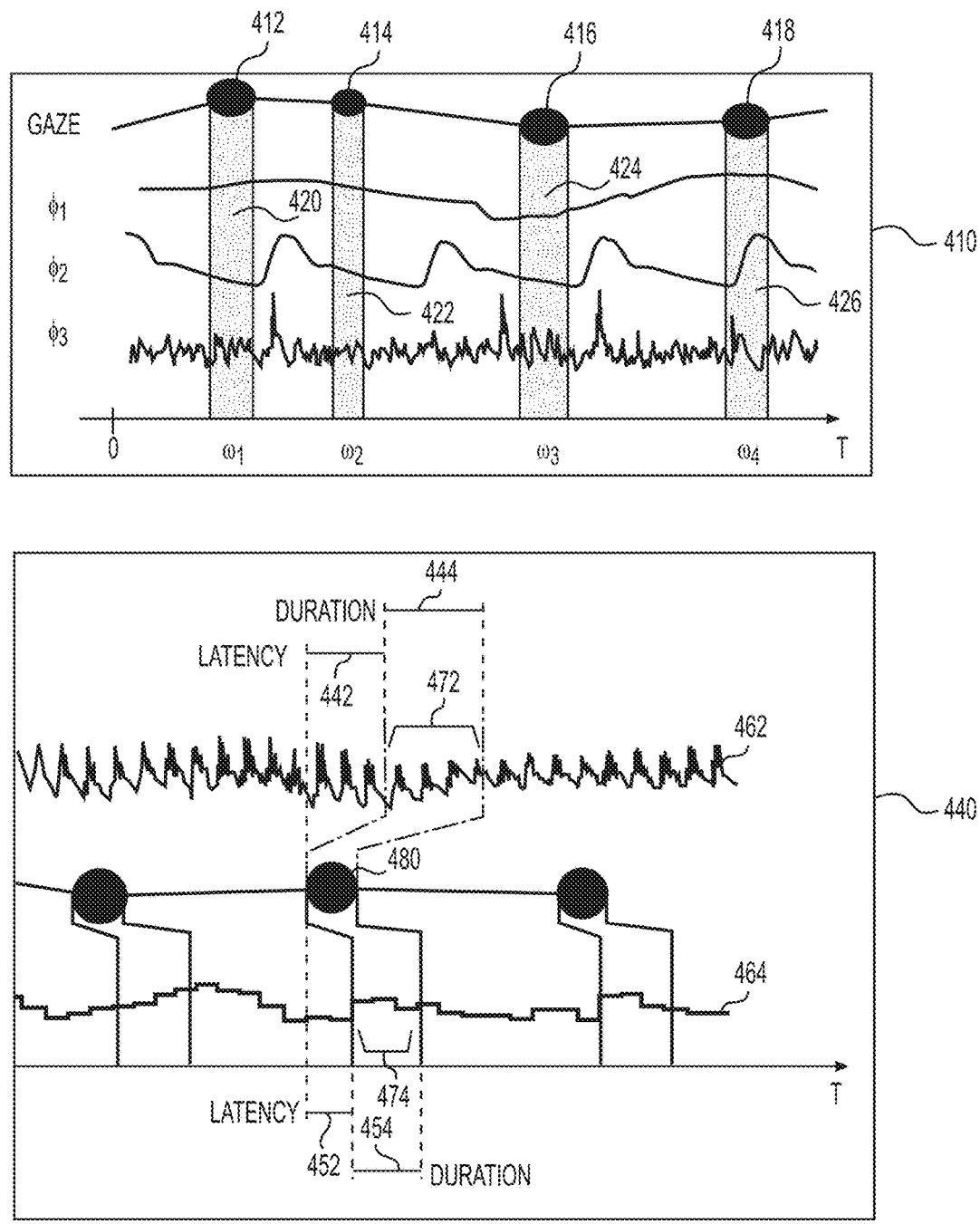
FIG. 3 represents diagrams of various physiological signals processed in accordance with an embodiment of the present technology.

Turning now to FIG. 3, diagrams of a various physiological signals processed in accordance with an embodiment of the present technology. FIG. 3 illustrates a first diagram 410 and a second diagram 440. The first diagram 410 illustrates positions 412, 414, 416 and 418. Each one of the positions 412, 414, 416 and 418 represents a particular position of a line of sight of a user of a time frame. The first diagram 410 also illustrates three physiological signals $\phi_1$, $\phi_2$, $\phi_3$ over the time frame. As an example, the physiological signal $\phi_1$ may be a heart rate, the physiological signal $\phi_2$ may be an electrodermal activity and the physiological signal $\phi_3$ may be a pupil size. In the example illustrated at FIG. 3, the positions 412, 414, 416 and 418 and the three physiological signals $\phi_1$, $\phi_2$, $\phi_3$ have been synchronised together so that they all share a same time frame (wherein t=0 is the same for the positions 412, 414, 416 and 418 and the three physiological signals $\phi_1$, $\phi_2$, $\phi_3$). The first diagram 410 also illustrates time segments 420, 422, 424 and 426 which, in some embodiments may represent a period of time during which the position of the line of sight is held by the user. The time segments 420, 422, 424 and 426 intersect the three physiological signals $\phi_1$, $\phi_2$, $\phi_3$. As an example, the time segment 420 identifies variations of the three physiological signals $\phi_1$, $\phi_2$, $\phi_3$ while the position 412 is held by the user.

As previously mentioned, because emotions and/or cognitions require physiological adjustments stemming from multiple responses patterns, different physiological signal may present various durations and/or latencies for a given stimulus. As a result, at least some physiological signals $\phi_1$, $\phi_2$, $\phi_3$ comprised in a time segment defined by a position may not correspond to emotions and/or cognitions resulting from a stimulus associated with the position. For example, in response to a stimulus, the hear rate may change more rapidly than electrodermal activity but more slowly than pupil size. Referring back to the example of FIG. 3, in response to the stimulus associated with a position, the physiological signal $\phi_1$ may start to vary before the physiological signal $\phi_2$ but after the physiological signal $\phi_3$.

Turning now to the second diagram 440, a first physiological signal 462 and a second physiological signal 464 are illustrated. As an example, the first physiological signal 462 may be a heart rate and the second physiological signal 464 may be a pupil size. The first physiological signal 462 may also be referred to as a first set of data associated with the first physiological signal 462. The second physiological signal 462 may also be referred to as a second set of data associated with the second physiological signal 462. The second diagram 440 also illustrates a first latency 442 and a first duration 444 associated with the first physiological signal 462 and a second latency 452 and a second duration 454 associated with the second physiological signal 464. The second diagram 440 also illustrates a position 480. The position 480 may be a position of a line of sight of a user from which the first physiological signal 462 and the second physiological signal 464 are sensed. In some embodiments, latency (such as the first latency 442 and the second latency 452) may be defined as time elapsed between a fixation onset (for example, associated with a position) and a beginning of a related physiological reaction reflected by a variation in a physiological signal. In some embodiments, duration (such as the first duration 444 and the second duration 4454) may be defined as time elapsed between a start and an end of a physiological reaction reflected by a variation in a physiological signal. The present technology therefore allows relying on specific extraction windows that may be optimized in terms of latency and duration for each physiological signal and/or for a given pattern category (for example, a given physiological construct).

Still referring to FIG. 3, for the position 480, a first subset of data 472 is identified from the first set of data based on the first latency 442 and the first duration 444. The first latency 442 and the first duration 444 may be associated with the physiological signal (and/or a category of the physiological signal such as heart rate, pupil size . . . ). In some embodiments, the first latency 442 and the first duration 444 may be dynamically determined based on a particular pattern category which is being assessed. For example, the pattern category may be a psychological construct of interest (e.g., an emotion, a cognitive load, a stress, an attention and/or a flow). A second subset of data 474 is also identified from the second set of data based on the second latency 442 and the second duration 444. The second latency 442 and the second duration 444 may be associated with the physiological signal (and/or a category of the physiological signal such as heart rate, pupil size . . . ). In some embodiments, as for the first latency 442 and the first duration 444, the second latency 452 and the second duration 454 may be dynamically determined based on a particular pattern category which is being assessed. In some embodiments, the first subset of data 472 and the second subset of data 474 are relied upon to generate a predicted value for a given position. In some embodiments, the predicted value may be associated with intensity and/or amplitude of a pattern (e.g., an emotion).

Figure 4:
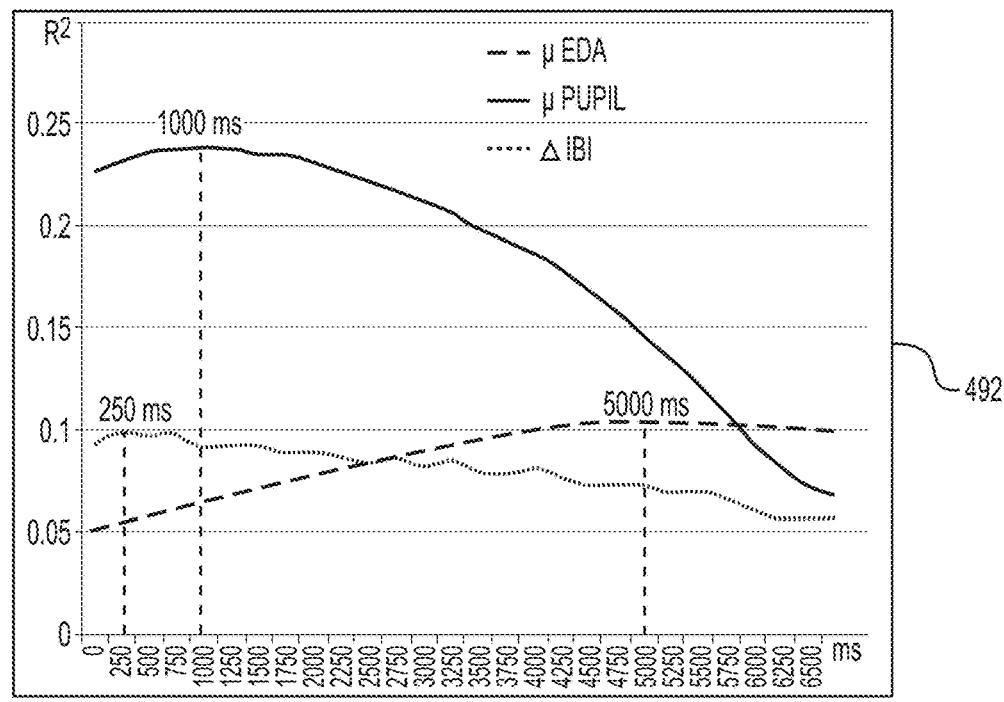
FIG. 4 is a diagram illustrating identification of latency and a duration to be used in accordance with an embodiment of the present technology.
Figure 4:
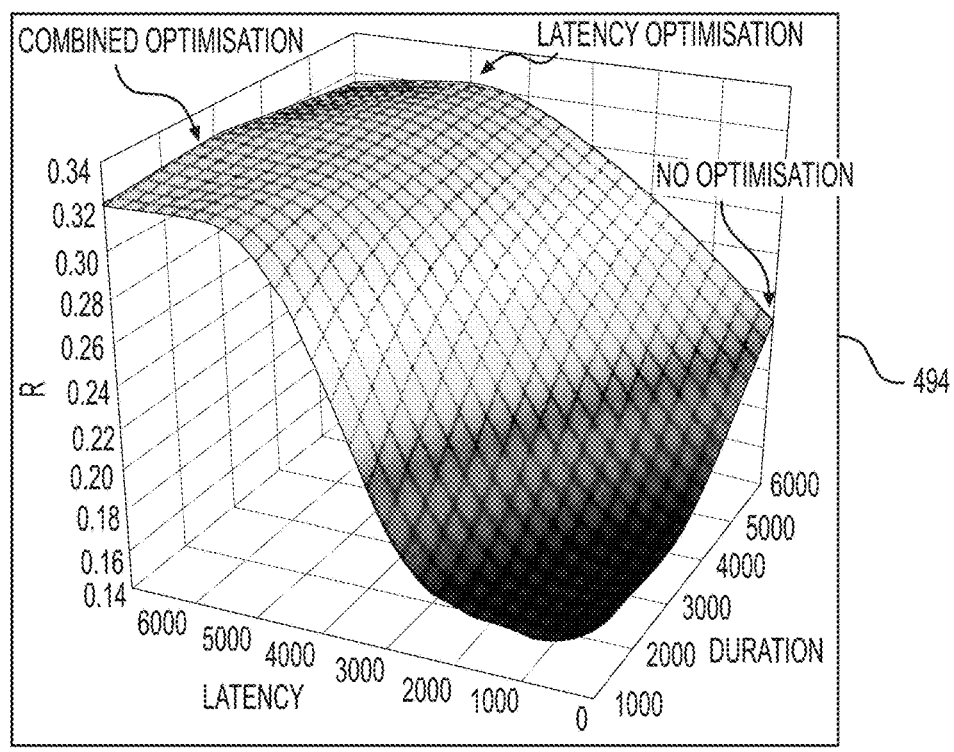

Turning now to FIG. 4, a diagram illustrates an example as to how latency (such as the first latency 442 and the second latency 452) and/or a duration (such as the first duration 444 and the second duration 454) may be determined. This example illustrates an example as to how latency and/or duration may be optimized for a particular physiological signal and/or pattern. In some embodiments, the latency and/or the duration may be generated based on an empirical optimization process. The empirical optimization process may be based on data previously stored, for example in the decision model database 304.

A first example 492 illustrates the optimisation of a latency of an attribute μ EDA for a construct of emotional arousal (which may also be referred to as a pattern). In this example, n=a number of data points in a training set and L=all possible latencies (e.g. between 0 and 7000 ms, in increments of 100 ms). For each latency Li, a table of size n×2 is generated containing n pairs [μ EDA, arousal] using an extraction window with latency Li. A Pearson correlation coefficient r2i is then computed between both columns of the table. The latency Li|max r2i may be selected as the optimal latency for the feature extraction window of μ EDA for emotional arousal. The first example 492 illustrates various latency values for three attributes (Δ interbeat interval, μ EDA, and μ pupil size), for the construct of emotional arousal. The latencies with the maximal r2 are identified with dotted lines (5000 ms for μ EDA, 250 ms for Δ IBI, and 1000 ms for μ Pupil).

As illustrated a second example 494, in order to simultaneously optimise both parameters of the extraction windows, the empirical optimisation process is extended to include duration. As illustrated in the second example 494 (for μ EDA), for each latency Li and each duration Dj, a correlation, such as, but not limited to, a Pearson correlation, coefficient rij may be computed. The previously obtained optimal latency, 5000 ms, goes up to 7000 ms when jointly optimised with duration for μ EDA.

As a person skilled in the art of the present technology may appreciate, in some embodiments, the latency and the duration may be independently determined (as it is the case in the first example 492) while, in some other embodiments, the latency and the duration may be dependently determined (as it is the case in the second example 494). It should also be appreciated that the first example 492 and second example 494 illustrate example of determination of the latency and duration, other variations may be envisioned without departing from the scope of the present technology.

Figure 5:
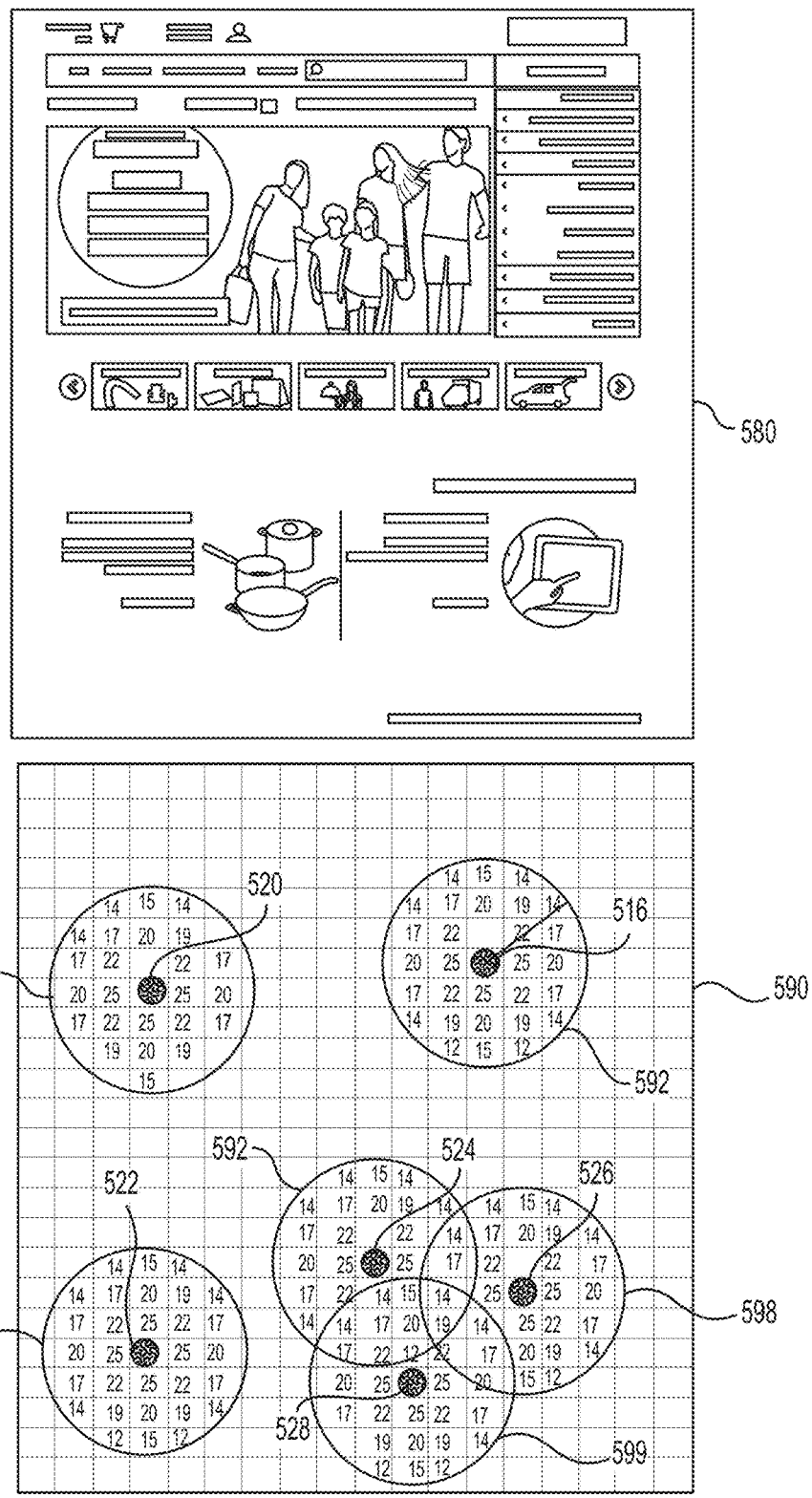
FIG. 5 is a diagram of a stimulus presented to a user along with a grid of pixels associated with predicted values generated in accordance with an embodiment of the present technology.

Turning now to FIG. 5, a representation of a stimulus 580 to be presented to a user is shown along with a grid of pixels 590. In this example, the stimulus 580 is a web page comprising various features, including various color patterns, textual information and various images. The grid of pixels 590 may be associated with stimulus 580. The grid of pixels may visually represent the stimulus 580. The grid of pixels 590 comprises multiple positions associated with a line of sight of a user. The multiple positions include a position 516 associated with surrounding values 592, a position 520 associated with surrounding values 594, a position 522 associated with surrounding values 596, a position 524 associated with surrounding values 592, a position 526 associated with surrounding values 598, a position 528 associated with surrounding values 599. The surrounding values 594, 596, 592, 598 and 599 may have been generated based on multiple predicted values, each one of which having been generated for a corresponding one of the positions 516, 520, 522, 524, 526 and 528. The surrounding values 594, 596, 592, 598 and 599 be generated based on the multiple predicted values and statistical distributions, such as, but not limited too, a Gaussian distribution.

Figure 6:
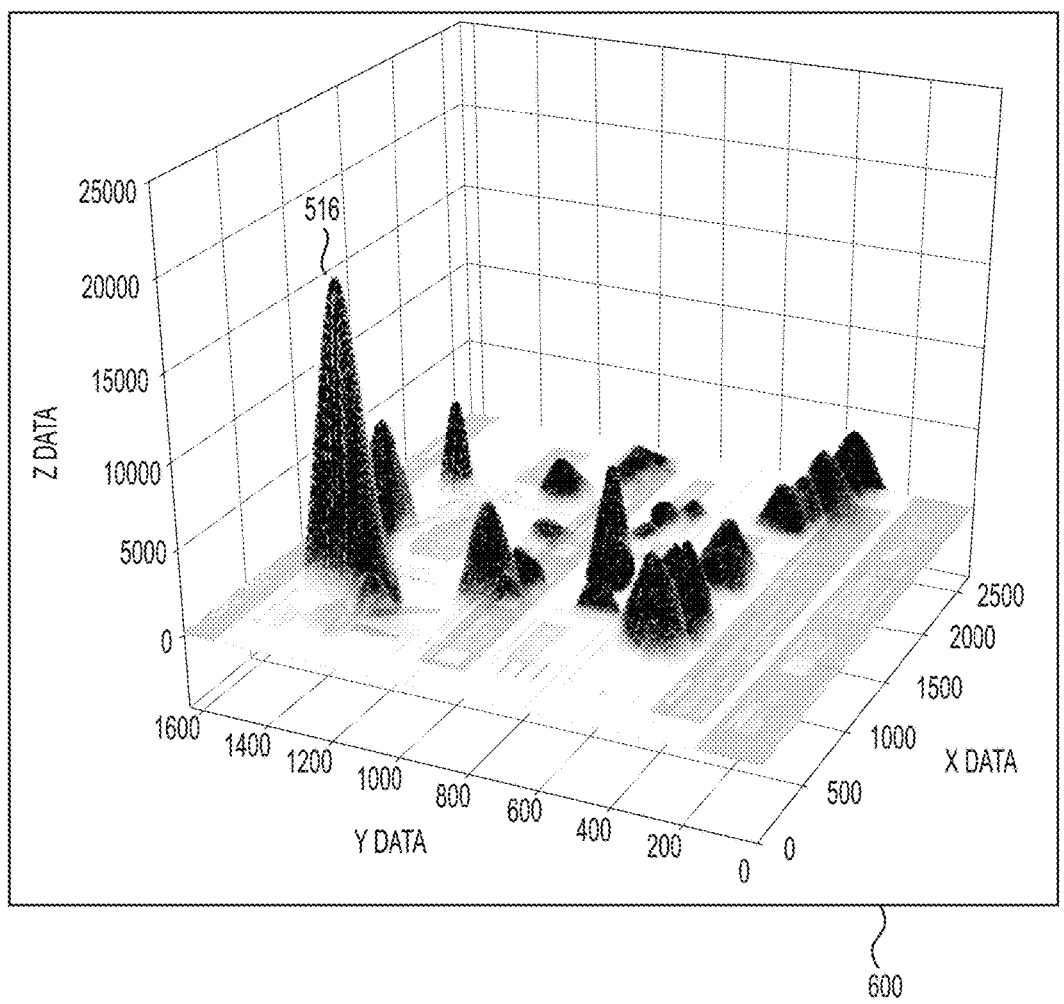
FIG. 6 is a diagram illustrating a heat map generated in accordance with an embodiment of the present technology.

FIG. 6 illustrates a heat map 600 generated in accordance with an embodiment of the present technology. The heat map 600 is generated from predicted values and surrounding values. In some embodiments, a peak may represent a sum of predicted values and the surrounding values define a surface associated with the peak. For example, the position 516 may be associated with a sum of predicted values which values are proportional to the height of the peak.

Figure 7:
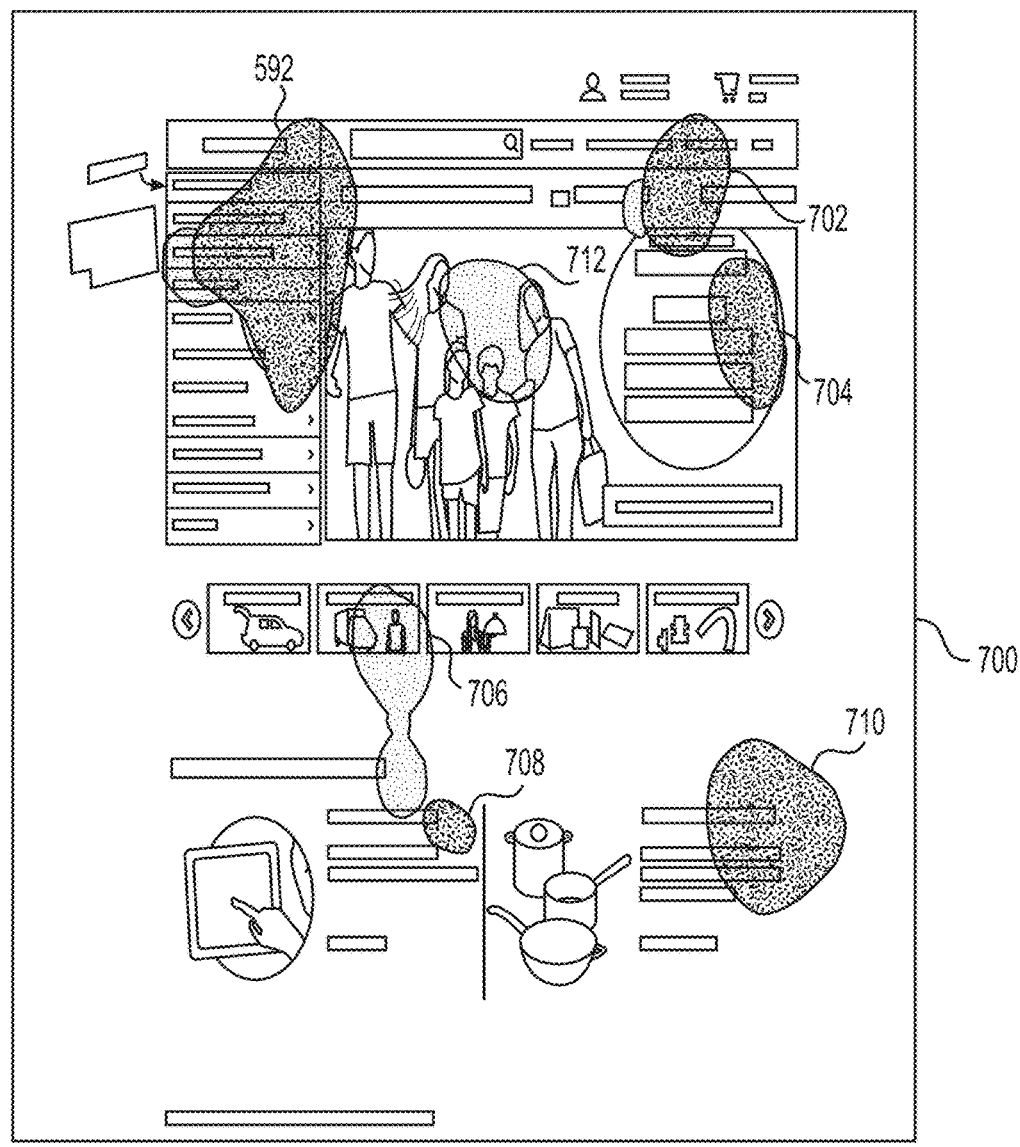
FIG. 7 is a diagram illustrating the stimulus of FIG. 5 superimposed with color patterns generated from the heat maps generated in accordance with an embodiment of the present technology.

FIG. 7 illustrates the stimulus of FIG. 5 superimposed with color patterns generated from the heat map of FIG. 6. For example, a color pattern 592 may be reflective of the position 516 and its associated surrounding values depicted at FIG. 6. The color pattern 592 includes variations of colors representative of variations of values. FIG. 7 also includes others color patterns 702, 704, 706, 708, 710 and 712 which colors and positions are based on a previously generated heat maps, such as the heat map of FIG. 6. In some embodiments, multiple heat maps, each of which being associated with a different pattern, may be superimposed with the stimulus. In some embodiments, each one of the different patterns may be represented by a different color.

As the reader may appreciate, FIG. 5-7 are provided as examples and should not be construed as being limitative. Multiple variants may be envisioned without departing from the scope of the present technology.

Given the architecture described with reference to FIG. 2 and the examples of FIG. 3-7, it is possible to execute a method of processing signals sensed from a user. The method can be, for example, but without being limitative, conveniently executable at the electronic device 310. To that extent, the electronic device 310 may comprise non-transitory computer usable information storage medium that enables the electronic device 310 to execute the method in accordance with embodiments of the present technology. For the sake of an example, the method 800 will be illustrated as executed on the electronic device 310.

Figure 8:
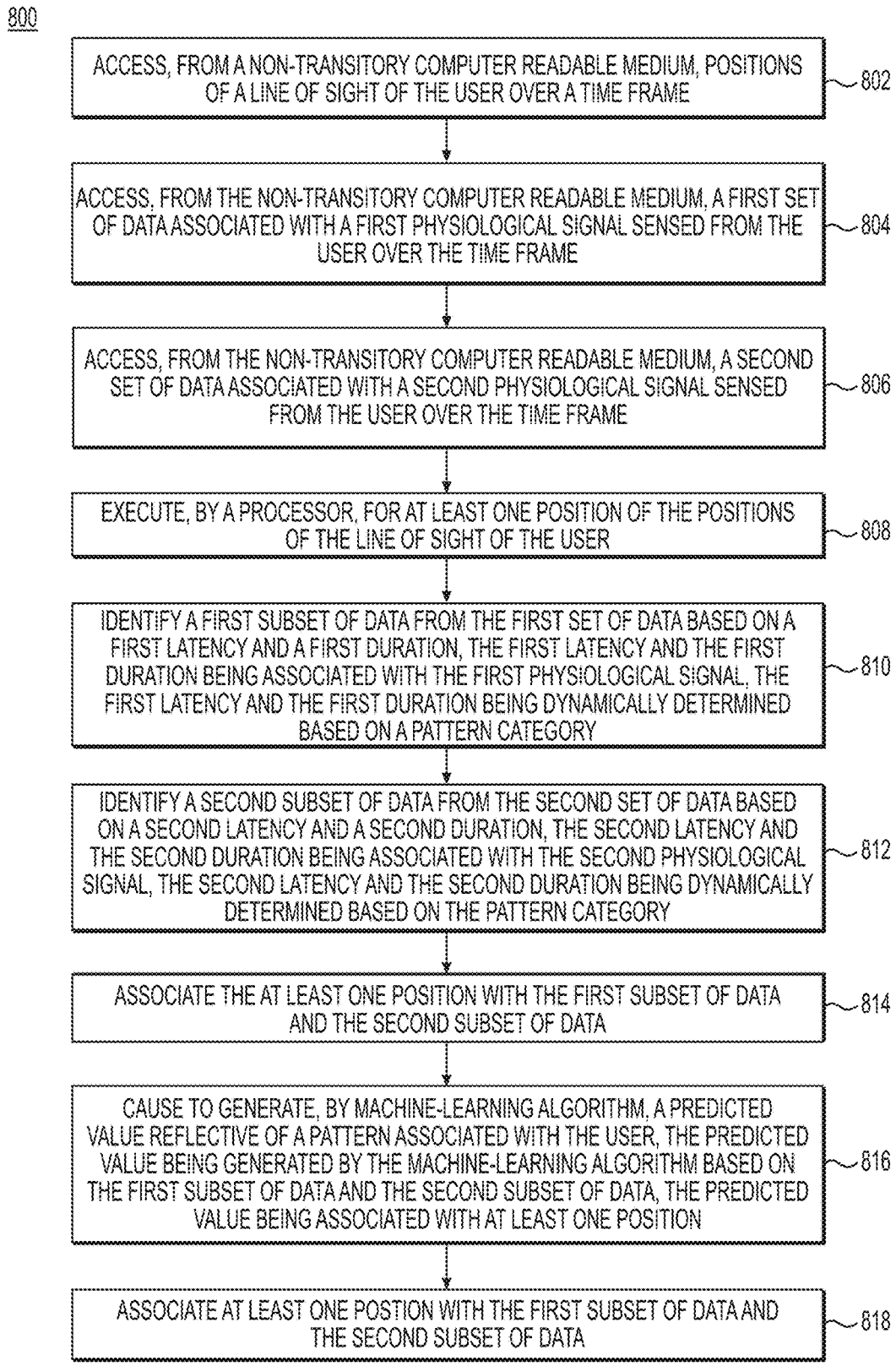
FIG. 8 is a flowchart illustrating a computer-implemented method implementing embodiments of the present technology.

More specifically, FIG. 8 shows a flowchart illustrating a computer-implemented method of 800 processing signals sensed from a user. The method 800 starts with step 802 accessing, from a non-transitory computer readable medium, positions of a line of sight of the user over a time frame.

Then, at a step 804, the method 800 accesses, from the non-transitory computer readable medium, a first set of data associated with a first physiological signal sensed from the user over the time frame. At step 806, the method 800 accesses, from the non-transitory computer readable medium, a second set of data associated with a second physiological signal sensed from the user over the time frame.

In some embodiments, the method 800 comprises synchronizing the first physiological signal, the second physiological signal and the at least one position. In some embodiments, the method 800 comprises (1) receiving, from a sensor, an eye tracking signal; and (2) generating, by the processor, the positions based on the eye tracking signal. In some embodiments, the method 800 comprises (1) receiving, from a first sensor, the first physiological signal; and (2) receiving, from a second sensor, the second physiological signal.

At step 808, the method 800 executes steps 810 to 818 for at least one position of the positions of the line of sight of the user. At step 810, the method 800 executes identifying a first subset of data from the first set of data based on a first latency and a first duration, the first latency and the first duration being associated with the first physiological signal, the first latency and the first duration being dynamically determined based on a pattern category. At step 812, the method 800 executes identifying a second subset of data from the second set of data based on a second latency and a second duration, the second latency and the second duration being associated with the second physiological signal, the second latency and the second duration being dynamically determined based on the pattern category. At step 814, the method 800 executes associating the at least one position with the first subset of data and the second subset of data.

At step 816, the method 800 executes causing to generate, by a machine-learning algorithm, a predicted value reflective of a pattern associated with the user, the predicted value being generated by the machine-learning algorithm based on the first subset of data and the second subset of data, the predicted value being associated with the at least one position. In some embodiments, causing to generate, by the machine-learning algorithm, the predicted value further comprises accessing a database comprising a set of data having been, at least partially, previously generated by the machine-learning algorithm. In some embodiments, at least one of the first subset of data and the second subset of data is compared, by the machine-learning algorithm, with the set of data to generate the predicted value. In some embodiments, the predicted value is reflective of at least one of intensity of the pattern and amplitude of the pattern. In some embodiments, executing, by the processor, the steps of identifying the first subset of data and identifying the second subset of data is carried out for each one of the positions of the line of sight of the user. In some embodiments, causing to generate, by the machine-learning algorithm, the predicted value reflective of the pattern associated with the user is carried out for each one of the positions of the line of sight of the user.

At step 818, the method 800 executes storing, in the non-transitory computer readable medium, the predicted value associated with the at least one position. In some embodiments, storing, in the non-transitory computer readable medium, the predicted value associated with the at least one position comprises storing, in the non-transitory computer readable medium, predicted values associated with corresponding positions.

In some embodiments, prior to identifying a first subset of data from the first set of data based on a first latency and a first duration, the method 800 comprises dynamically determining the pattern category. In some embodiments, at least one position is associated with a pixel of a screen. In some embodiments, the method 800 further comprises, generating, by the processor, a set of surrounding predicted values based on the predicted value, each one of the surrounding value of the set of surrounding values being associated with a corresponding pixel surrounding the pixel associated with the at least one position. In some embodiments, the set of surrounding predicted values is generated based on a statistical distribution.

In some embodiments, the method 800 further comprises generating, by the processor, a heat map representing the predicted values, each one of the predicted values being positioned on the heat map based on its corresponding position. In some embodiments, the pattern is a psychological construct and the pattern category is a category of psychological construct.

While the above-described implementations have been described and shown with reference to particular steps performed in a particular order, it will be understood that these steps may be combined, sub-divided, or re-ordered without departing from the teachings of the present technology. Accordingly, the order and grouping of the steps is not a limitation of the present technology.

It should be expressly understood that not all technical effects mentioned herein need to be enjoyed in each and every embodiment of the present technology. For example, embodiments of the present technology may be implemented without the user enjoying some of these technical effects, while other embodiments may be implemented with the user enjoying other technical effects or none at all.

Some of these steps and signal sending-receiving are well known in the art and, as such, have been omitted in certain portions of this description for the sake of simplicity. The signals can be sent-received using optical means (such as a fibre-optic connection), electronic means (such as using wired or wireless connection), and mechanical means (such as pressure-based, temperature based or any other suitable physical parameter based).

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

What is claimed is:

1. A computer-implemented method of processing signals sensed from a user, the method comprising:
   accessing, from a non-transitory computer readable medium, positions of a line of sight of the user over a time frame;
   accessing, from the non-transitory computer readable medium, a first set of data associated with a first physiological signal sensed from the user over the time frame;
   accessing, from the non-transitory computer readable medium, a second set of data associated with a second physiological signal sensed from the user over the time frame;
   executing, by a processor, for at least one position of the positions of the line of sight of the user:
      identifying a first subset of data from the first set of data based on a first latency and a first duration, the first latency and the first duration being associated with the first physiological signal, the first latency and the first duration being dynamically determined based on a pattern category;
      identifying a second subset of data from the second set of data based on a second latency and a second duration, the second latency and the second duration being associated with the second physiological signal, the second latency and the second duration being dynamically determined based on the pattern category;
      associating the at least one position with the first subset of data and the second subset of data;
      causing to generate, by a machine-learning algorithm, a predicted value reflective of a pattern associated with the user, the predicted value being generated by the machine-learning algorithm based on the first subset of data and the second subset of data, the predicted value being associated with the at least one position; and
      storing, in the non-transitory computer readable medium, the predicted value associated with the at least one position.

2. The method of claim 1, wherein prior to identifying a first subset of data from the first set of data based on a first latency and a first duration, the method comprises determining the pattern category.

3. The method of claim 1, wherein causing to generate, by the machine-learning algorithm, the predicted value further comprises accessing a database comprising a set of training data having been, at least partially, previously generated by the machine-learning algorithm.

4. The method of claim 3, wherein at least one of the first subset of data and the second subset of data is compared, by the machine-learning algorithm, with the set of training data to generate the predicted value.

5. The method of claim 1, wherein the predicted value is reflective of at least one of an intensity of the pattern and amplitude of the pattern.

6. The method of claim 1, wherein the at least one position is associated with a pixel of a screen.

7. The method of claim 1, wherein the method further comprises, generating, by the processor, a set of surrounding predicted values based on the predicted value, each one of the surrounding value of the set of surrounding values being associated with a corresponding pixel surrounding the pixel associated with the at least one position.

8. The method of claim 1, wherein executing, by the processor, the steps of identifying the first subset of data and identifying the second subset of data is carried out for each one of the positions of the line of sight of the user.

9. The method of claim 8, wherein causing to generate, by the machine-learning algorithm, the predicted value reflective of the pattern associated with the user is carried out for each one of the positions of the line of sight of the user.

10. The method of claim 1, wherein the method further comprises generating, by the processor, a heat map representing the predicted values, each one of the predicted values being positioned on the heat map based on its corresponding position.

11. The method of claim 1, wherein, prior to executing, by the processor, the steps of identifying the first subset of data and identifying the second subset of data, the method comprises synchronizing the first physiological signal, the second physiological signal and the at least one position.

12. The method of claim 1, wherein prior to accessing, from the non-transitory computer readable medium, the positions of the line of sight of the user over the time frame, the method comprises (1) receiving, from a sensor, an eye tracking signal; and (2) generating, by the processor, the positions based on the eye tracking signal.

13. The method of claim 1, wherein prior to accessing, from the non-transitory computer readable medium, the positions of the line of sight of the user over a time frame, the method comprises (1) receiving, from a first sensor, the first physiological signal; and (2) receiving, from a second sensor, the second physiological signal.

14. A computer-implemented system for processing signals sensed from a user, the system comprising:
a non-transitory computer-readable medium;
a processor configured to perform:
accessing, from the non-transitory computer readable medium, positions of a line of sight of the user over a time frame;
accessing, from the non-transitory computer readable medium, a first set of data associated with a first physiological signal sensed from the user over the time frame;
accessing, from the non-transitory computer readable medium, a second set of data associated with a second physiological signal sensed from the user over the time frame;
executing, by the processor, for at least one position of the positions of the line of sight of the user:
identifying a first subset of data from the first set of data based on a first latency and a first duration, the first latency and the first duration being associated with the first physiological signal, the first latency and the first duration being dynamically determined based on a pattern category;
identifying a second subset of data from the second set of data based on a second latency and a second duration, the second latency and the second duration being associated with the second physiological signal, the second latency and the second duration being dynamically determined based on the pattern category;
associating the at least one position with the first subset of data and the second subset of data;
causing to generate, by a machine-learning algorithm, a predicted value reflective of a pattern associated with the user, the predicted value being generated by the machine-learning algorithm based on the first subset of data and the second subset of data, the predicted value being associated with the at least one position; and
storing, in the non-transitory computer readable medium, the predicted value associated with the at least one position.

15. The system of claim 14, wherein the predicted value is reflective of at least one of an intensity of the pattern and amplitude of the pattern.

16. The system of claim 14, wherein the processor is further configured to cause: generating a set of surrounding predicted values based on the predicted value, each one of the surrounding value of the set of surrounding values being associated with a corresponding pixel surrounding the pixel associated with the at least one position.

17. The system of claim 14, wherein executing, by the processor, the steps of identifying the first subset of data and identifying the second subset of data is carried out for each one of the positions of the line of sight of the user.

18. The system of claim 14, wherein the processor is further configured to cause, prior to executing, by the processor, the steps of identifying the first subset of data and identifying the second subset of data, synchronizing the first physiological signal, the second physiological signal and the at least one position.

19. The system of claim 14, wherein the processor is further configured to cause, prior to accessing, from the non-transitory computer readable medium, the positions of the line of sight of the user over the time frame, (1) receiving, from a sensor, an eye tracking signal; and (2) generating, by the processor, the positions based on the eye tracking signal.

20. The system of claim 14, wherein the processor is further configured to cause, prior to accessing, from the non-transitory computer readable medium, the positions of the line of sight of the user over a time frame, (1) receiving, from a first sensor, the first physiological signal; and (2) receiving, from a second sensor, the second physiological signal.

* * * * *